US00PP27931P3

(12) United States Plant Patent
Growns

(10) Patent No.: US PP27,931 P3
(45) Date of Patent: Apr. 25, 2017

(54) ***GREVILLEA* PLANT NAMED 'KINGS RAINBOW'**

(50) Latin Name: ***Grevillea* hybrid**
Varietal Denomination: Kings Rainbow

(71) Applicant: Botanic Gardens and Parks Authority, West Perth (AU)

(72) Inventor: Digby Growns, Canning Vale (AU)

(73) Assignee: Botanic Gardens and Parks Authority, West Perth (AU)

( * ) Notice: Subject to any disclaimer, the term of this patent is extended or adjusted under 35 U.S.C. 154(b) by 0 days.

(21) Appl. No.: 14/998,686

(22) Filed: Feb. 2, 2016

(65) Prior Publication Data

US 2016/0345479 P1 Nov. 24, 2016

Related U.S. Application Data

(60) Provisional application No. 62/230,011, filed on May 22, 2015.

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Annette Para
(74) *Attorney, Agent, or Firm* — Audrey Charles

(57) ABSTRACT

A new and distinct cultivar of *Grevillea* plant named 'Kings Rainbow', characterized by its light yellow-green and medium red bi-colored, medium green-colored foliage, and moderately vigorous, semi-upright growth habit, is disclosed.

1 Drawing Sheet

Latin name of genus and species of plant claimed: *Grevillea* hybrid.

Variety denomination: 'Kings Rainbow'.

BACKGROUND OF THE INVENTION

The present invention relates to a new and distinct cultivar of *Grevillea* plant botanically known as *Grevillea* hybrid and hereinafter referred to by the cultivar name 'Kings Rainbow'.

The new cultivar originated in a controlled breeding program in West Perth, Australia during May 2010. The objective of the breeding program was the development of *Grevillea* cultivars that have large inflorescences with attractive colors.

The new *Grevillea* cultivar is the result of cross-pollination. The female (seed) parent of the new cultivar is a *Grevillea armigera* proprietary breeding selection not coded, not patented, characterized by its yellow-green and dark burgundy to black colored inflorescences, medium green-colored foliage, and moderately vigorous, semi-upright growth habit. The male (pollen) parent of the new cultivar is a *Grevillea* hybrid proprietary breeding selection coded 20101122, not patented, characterized by its medium red-colored inflorescences, medium green-colored foliage, and vigorous, upright growth habit. The new cultivar was discovered and selected as a single flowering plant within the progeny of the above stated cross-pollination during September 2011 in a controlled environment in in West Perth, Australia.

Asexual reproduction of the new cultivar by terminal stem cuttings since September 2011 in West Perth Australia and Valley Center, Calif. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Kings Rainbow' as a new and distinct cultivar of *Grevillea* plant:

1. Light yellow-green and medium red bi-colored inflorescences;
2. Medium green-colored foliage; and
3. Moderately vigorous, semi-upright growth habit.

Plants of the new cultivar differ from plants of the female parent primarily in inflorescence color and from plants of the male parent primarily in inflorescence color and growth habit.

Of the many commercially available *Grevillea* cultivars, the most similar in comparison to the new cultivar is 'Red Hooks', not patented. However, in side-by-side comparison, plants of the new cultivar differ from plants of 'Red Hooks' in at least the following characteristics:

1. Plants of the new cultivar have a leaf shape different from plants of 'Red Hooks';
2. Plants of the new cultivar have a bud color different from plants of 'Red Hooks'; and
3. Plants of the new cultivar have an inflorescence color that is a shade of red different from plants of 'Red Hooks'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Kings Rainbow'. The plants are approximately two-years old and were grown in three-gallon containers for approximately 17 months in an outdoor nursery in Valley Center, Calif. Plants were given two pinches during the 17 month growth period.

DETAILED BOTANICAL DESCRIPTION

Figure 1:
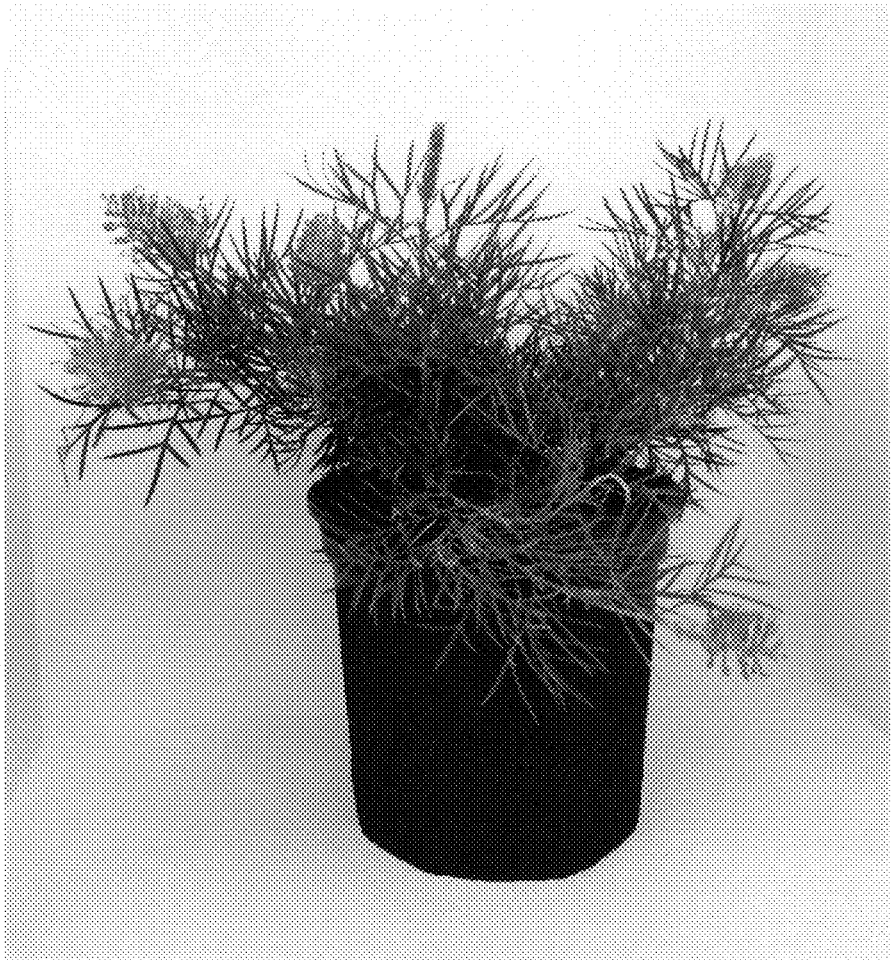
FIG. 1 illustrates a side view of the overall growth and flowering habit of 'Kings Rainbow'.
Figure 2:
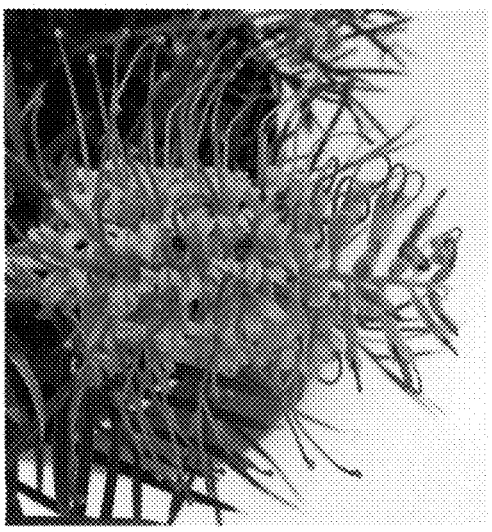
FIG. 2 illustrates a close-up view of the inflorescences of 'Kings Rainbow'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in January 2016 under natural light conditions in West Chicago, Ill.

The following descriptions and measurements describe two-year old plants produced from cuttings from stock plants and grown in an outdoor nursery in Valley Center, Calif. Temperatures for this period ranged from 72° F. to 78° F. (22° C. to 26° C.) during the day to 52° F. to 58° F. (11° C. to 14° C.) during the night. The plants were grown in three-gallon containers for approximately 17 months utilizing a soilless growth medium. Plants were given two pinches during the 17 month growth period. Measurements and numerical values represent averages of typical plants.

Botanical classification: *Grevillea* hybrid cultivar Kings Rainbow.

Parentage:

*Female parent.*—*Grevillea armigera* proprietary breeding selection not coded, not patented.

*Male parent.*—*Grevillea* hybrid proprietary breeding selection coded 20101122, not patented.

Propagation:

*Type cutting.*—Terminal stem.

*Time to initiate roots.*—Approximately 12 to 16 weeks.

*Time to produce a rooted cutting.*—Approximately 20 to 24 weeks.

*Root description.*—Light brown in color, fine.

*Rooting habit.*—Freely branching, tight groupings of small rootlets.

Plant description:

*Commercial crop time.*—Approximately 16 to 24 weeks from a rooted cutting to finish in a one-gallon container.

*Growth habit and general appearance.*—Moderately vigorous, upright.

*Size.*—Height from soil level to top of plant plane: Approximately 30.0 cm. Width: Approximately 46.0 cm.

*Branching habit.*—Freely branching, pinching enhances branching. Quantity of main branches per plant: Approximately 1 trunk with 6 branches.

*Branch.*—Strength: Strong. Length to base of peduncle: Approximately 18.0 cm. Diameter: Approximately 4.0 mm. Length of central internode: Approximately 2.0 cm. Texture: Tomentose. Pubescence color: NN155D with 199B. Color of young stems: 146B, color appears light brown due to pubescence. Color of mature stems: 199A with N200B.

Foliage description:

*General description.*—Form: Simple. Arrangement: Alternate. Fragrance: None detected.

*Leaves.*—Aspect: Acute angle to stem. Shape: 6 to 8 lobed, lobes linear and clustered nearest apex. Margin: Entire, pinnatisect; leaf margins curve downwards enclosing the lower surface of the leaf. Apex of lobes: Acute. Base: Narrowly attenuate. Venation pattern: Pinnate. Length of mature leaf: Approximately 8.0 cm. Width of mature leaf: Approximately 6.5 cm. Texture of upper surface: Immature leaves moderately pubescent, scattered silky hairs, becomes sparsely pubescent with development. Texture of lower surface: Tomentose with the exception of midvein. Pubescence color: NN155D. Color of upper surface of young foliage: 137B mixed with 144A, color appears slightly lighter due to pubescence, indistinguishable venation. Color of lower surface of young foliage: Closest to 137C mixed with 144A, color appears slightly lighter due to pubescence, indistinguishable venation. Color of upper surface of mature foliage: 137A, lobe tips tinted with 187A, venation indistinguishable. Color of lower surface of mature foliage: 138A, color appears slightly lighter due to pubescence, indistinguishable venation.

Flowering description:

*Flowering habit.*—'Kings Rainbow' is freely flowering under outdoor growing conditions with substantially continuous blooming in Zones 9*a* through 11.

*Lastingness of individual inflorescence on the plant.*—Approximately 3 weeks.

Inflorescence description:

*General description.*—Type: Raceme. Self-cleaning. Shape: Cylindrical conflorescence. Aspect: Facing upward and outward. Arrangement: Terminal and from leaf axils. Fragrance: None detected. Quantity per plant: Approximately 5. Diameter: Approximately 7.0 cm. Depth: Approximately 6.5 cm.

*Bud.*—Rate of opening: Generally takes 4 to 6 days for bud to progress from first color to fully open floret.

*Bud just before opening.*—Shape: Globular. Diameter: Approximately 3.0 mm. Texture of outer surface: Tomentose. Pubescence color: NN155D. Color: 154C appears lighter due to pubescence.

*Florets.*—Quantity per inflorescence: Approximately 80. Arrangement: Primarily in pairs. Length: Approximately 3.2 cm. Diameter: Approximately 7.0 mm.

*Perianth.*—Shape: Tubular with a ventral limb, becomes revolute during anthesis. Length: Approximately 9.0 mm. Diameter at widest point: Approximately 7.0 mm. Diameter at base: Approximately 2.0 mm.

*Tepals.*—Quantity: 4. Shape: Linear. Margin: Entire. Apex: Acute. Length: Approximately 9.0 mm. Width: Approximately 2.0 mm. Texture of outer surface: Tomentose. Pubescence color: NN155D. Texture of inner surface: Glabrous. Color of outer surface when fully open: 145C, appears to be a lighter color due to pubescence. Color of inner surface when fully open: Closest to 154D.

*Peduncle*.—Strength: Strong. Aspect: Erect. Length: Approximately 1.5 cm. Diameter: Approximately 3.0 mm. Texture: Tomentose. Pubescence color: NN155D with 199B. Color: 146B, color appears light brown due to pubescence.

*Rachis*.—Strength: Strong. Length: Approximately 6.0 cm. Diameter: Approximately 3.0 mm. Texture of outer surface: Tomentose. Pubescence color: NN155D. Color: 146B appears lighter due to pubescence.

*Pedicel*.—Strength: Strong. Aspect: Erect. Length: Approximately 4.0 mm. Diameter: Approximately 1.0 mm. Texture of outer surface: Tomentose. Pubescence color: NN155D. Color: 145C appears lighter due to pubescence.

*Reproductive organs*.—Androecium: Anthers located within perianth limb and basally attached to perianth. Anther quantity: 4 per floret. Anther shape: Bilobed. Anther length: Approximately 1.0 mm. Anther color: 187A with surface facing tepals of 146B. Pollen amount: Sparse. Pollen color: 163D. Gynoecium: Stigma functions as a pollen presenter holding pollen for pollinators to remove until stigma matures becoming receptive to cross pollination. Nectary located at base of ovary. Pistil quantity: 1 per floret. Pistil length: Approximately 3.2 cm. Stigma shape: Funnel. Stigma length: Less than 1 mm. Stigma color: 163A. Style length: Approximately 3.0 cm. Style color: 145B at base transitioning to 53A at stigma. Ovary length: Approximately 2.0 mm. Ovary texture: Tomentose. Pubescence color: NN155D. Ovary color: 145D, appears white due to pubescence. Nectary size: Approximately 1.0 mm in length and 2.0 mm in width. Nectary color: 145A.

Seed and fruit production: Neither seed nor fruit production has been observed.

Disease and pest resistance: Resistance to pathogens and pests common to *Grevillea* has not been observed.

What is claimed is:

1. A new and distinct cultivar of *Grevillea* plant named 'Kings Rainbow', substantially as herein illustrated and described.

* * * * *